United States Patent

Kaschig et al.

Patent Number: 5,241,109
Date of Patent: Aug. 31, 1993

[54] ASYMMETRICAL OXALIC ACID DIARYLAMIDE

[75] Inventors: Jürgen Kaschig, Freiburg, Fed. Rep. of Germany; Gerhard Reinert, Allschwil, Switzerland; Georges Metzger, Moernach, France

[73] Assignee: Ciba-Geigy Corporation, Ardsley, N.Y.

[21] Appl. No.: 858,913

[22] Filed: Mar. 27, 1992

[30] Foreign Application Priority Data

Apr. 3, 1991 [CH] Switzerland ............... 987/91
Feb. 5, 1992 [CH] Switzerland ............... 325/92

[51] Int. Cl.$^5$ ............... C07C 381/14
[52] U.S. Cl. ............... 562/42; 562/48; 562/52
[58] Field of Search ............... 562/42, 48, 52

[56] References Cited

U.S. PATENT DOCUMENTS

| | | | |
|---|---|---|---|
| 3,529,982 | 9/1970 | Linethi et al. | 427/160 |
| 3,542,573 | 11/1970 | Biland et al. | 106/186 |
| 4,003,875 | 1/1977 | Luthi et al. | 554/5 |

*Primary Examiner*—José G. Dees
*Assistant Examiner*—Joseph M. Conrad
*Attorney, Agent, or Firm*—Marla J. Mathias; George R. Dohmann

[57] ABSTRACT

There is disclosed a water-soluble, asymmetrical oxalic acid diarylamide of general formula

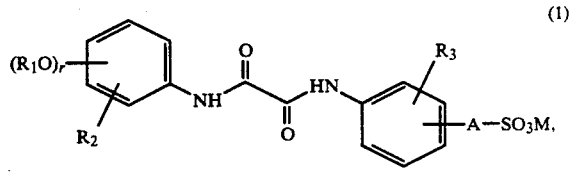

(1)

wherein the substituents
$R_1$ are each independently of the other unsubstituted or hydroxy- or alkoxy-substituted $C_1$–$C_5$alkyl, unsubstituted or $C_1$–$C_5$alkyl-substituted benzyl,
$R_2$ is hydrogen, halogen, $C_1$–$C_{12}$alkyl or phenyl-$C_1$–$C_5$alkyl,
$R_3$ is hydrogen, halogen, $C_1$–$C_{12}$alkyl, phenyl-$C_1$–$C_5$alkyl or $C_1$–$C_5$alkoxy,
A is a direct bond or a divalent radical of formula —O—Q—, wherein
Q is unsubstituted or hydroxy-substituted $C_1$–$C_6$alkylene,
M is hydrogen or alkali metal, and
r is 2, 1 or 0.

The novel water-soluble compound having fiber affinity is suitable for the photochemical and thermal stabilisation of polyamide fiber materials and the dyeings produced thereon.

7 Claims, No Drawings

ASYMMETRICAL OXALIC ACID DIARYLAMIDE

The present invention relates to a novel water-soluble, asymmetrical oxalic acid diarylamide and to the use thereof for the photochemical and thermal stabilisation of natural and synthetic polyamide fibres an the dyeings produced thereon.

Oxalic acid diarylamides which contain sulfo groups are disclosed, inter alia, in U.S. Pat. Nos. 3,529,982, 4,003,875 and 3,542,573. Asymmetrical oxalic acid diarylamides are disclosed in the first two references, and symmetrical ones are disclosed in the third reference. The drawback of these compounds is, however, that they exhaust less well onto polyamide fibres.

Surprisingly, it has now been found that appropriate choice of substituents which carry sulfo groups makes it possible to prepare an asymmetrical oxalic acid diarylamide which is water-soluble and has fibre affinity. It is therefore suitable for use as photochemical stabiliser for natural and synthetic polyamide fibres and the dyeings produced thereon, and can be used in all standard dyeing processes and after treatments to obtain good wetfastness properties.

Specifically, the invention relates to a water-soluble, asymmetrical oxalic acid diarylamide of general formula

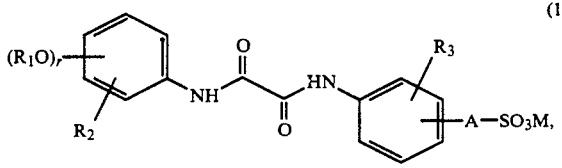

(1)

wherein the substituents
  $R_1$ are each independently of the other unsubstituted or hydroxy- or alkoxy-substituted $C_1$-$C_5$alkyl, unsubstituted or $C_1$-$C_5$alkyl-substituted benzyl,
  $R_2$ is hydrogen, halogen, $C_1$-$C_{12}$alkyl or phenyl-$C_1$-$C_5$alkyl,
  $R_3$ is hydrogen, halogen, $C_1$-$C_{12}$alkyl, phenyl-$C_1$-$C_5$alkyl or $C_1$-$C_5$alkoxy,
  A is a direct bond or a divalent radical of formula —O—Q—, wherein
  Q is unsubstituted or hydroxy-substituted $C_1$-$C_6$alkylene,
  M is hydrogen or alkali metal, and
  r is 2, 1 or 0.

In the definition of the substituents $R_1$ to $R_3$, $C_1$-$C_5$alkyl and $C_1$-$C_5$alkoxy denote those groups or moieties which contain 1 to 5, preferably 1 to 3 carbon atoms. Such groups are typically methyl, ethyl, n-propyl, isopropyl, n-butyl, sec-butyl, tert-butyl, amyl or isoamyl and, respectively, methoxy, ethoxy, isopropoxy, isobutoxy, tert-butoxy or tert-amyloxy.

$R_2$ and $R_3$ defined as $C_1$-$C_{12}$alkyl may be branched or unbranched radicals, for example those defined in respect of $C_1$-$C_5$alkyl as well as alkyl groups containing a greater number of carbon atoms, typically pentyl, neopentyl, tert-pentyl, hexyl, isohexyl, heptyl, octyl, isooctyl, nonyl, decyl, undecyl or dodecyl.

Q defined as $C_1$-$C_6$alkylene is a divalent saturated hydrocarbon radical such as methylene, ethylene, propylene, trimethylene, tetramethylene, ethylethylene, pentamethylene or hexamethylene.

Phenyl-$C_1$-$C_5$alkyl may be phenethyl, phenylpropyl, phenylbutyl or, preferably, benzyl.

Halogen is fluoro, bromo or chloro. Chloro is preferred.

Alkali metals may conveniently be lithium, sodium or potassium. Sodium is preferred.

A preferred compound of formula (1) is one wherein Q is trimethylene or

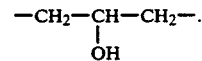

A further preferred oxalic acid diarylamide is that of formula

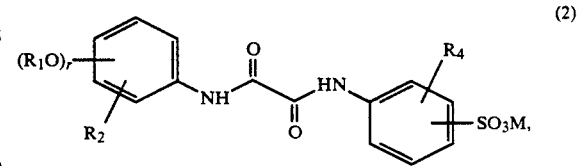

(2)

wherein
  $R_4$ is $C_1$-$C_{12}$alkyl or $C_1$-$C_5$alkoxy, and
  $R_1$, $R_2$, M and r are as defined for formula 1.

A compound meriting particular interest is that of formula

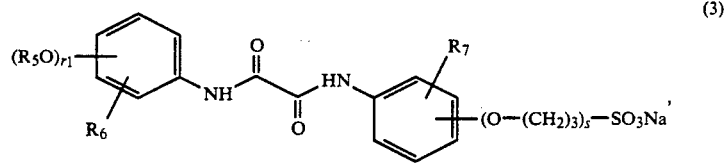

(3)

wherein
  $R_5$ is $C_1$-$C_3$alkyl,
  $R_6$ is hydrogen or $C_1$-$C_3$alkyl,
  $R_7$ is hydrogen or $C_1$-$C_3$alkoxy
  $r_1$ is 0, 1 or 2, and
  s is 0 or 1.

A particularly preferred compound of the above formula is that wherein
  $R_5$ is ethyl and
  $R_6$ is hydrogen or ethyl.

To be singled out for special mention is the compound of formula

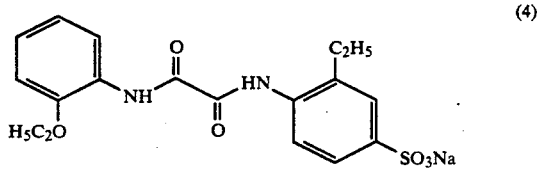

(4)

The asymmetrical oxalic acid diarylamide of general formula (1) is prepared by methods which are known per se, for example as described in U.S. Pat. No. 8,529,982. The compound is obtained by amidating, in the first step, oxalic acid or an ester thereof in per se known manner by the partial reaction of oxalic acid or an ester thereof, preferably an alkyl ester, with an approximately equimolar amount of the corresponding aniline. A preferred method typically comprises condensing oxalic acid, the partial ester or diester of oxalic acid carrying similar or different ester groups with an approximately molar amount of the aniline compound in the melt or in organic solvents which are inert to the reactants, in the presence of anhydrous boric acid and in the temperature range from about 50° to 200° C. After isolation of the resultant amide ester or amide acid, the still remaining carboxyl or carboxylate group of the oxalic acid partial amide is condensed under similar conditions with a second aniline which differs from that of the first step, conveniently choosing a temperature range which is 50° to 100° C. higher and is in the range from about 100° to 250° C.

Suitable insert organic solvents mentioned above are preferably those whose boiling point is above c. 160° C., i.e. conveniently higher aromatic hydrocarbons or halogenated hydrocarbons such as dichlorobenzene or trichlorobenzene.

The introduction of the second amide group can alternatively also be effected by partial saponification of the amide ester obtained in the first step to the amide acid, converting said amide acid into the amide acid halide and subsequently amidating the acid halide group.

The oxalic acid diarylamide so obtained which still contains free hydroxyl groups is subsequently etherified in known manner.

The novel asymmetrical oxalic acid diarylamide is used for the photochemical and thermal stabilisation of natural and synthetic polyamide fibre materials and the dyeings produced thereon. In application it is distinguished by superior light stability and good fibre affinity, and imparts enhanced photochemical stability to the fibre materials treated with these compounds. In natural polyamide fibres, especially in wool, the enhanced photostability takes the form of a stabilisation of the original whiteness of the fibre.

Polyamide fibre material will be understood as meaning in the context of this invention synthetic polyamide, typically polyamide 6, polyamide 66 or also polyamide 12 as well as wool and silk. In addition to pure polyamide fibres, fibre blends such as polyamide 6/wool or polyurethane/polyamide blends, for example tricot material made from polyamide/polyurethane in the ratio 70:30, are also suitable. Polypropylene/polyamide blends can also suitably be used. In principle, the pure polyamide material or blends thereof may be in various forms of presentation, including fibres, yarn, woven fabrics, knitted fabrics or carpets.

The inventive compounds are particularly suitable for application to polyamide material and blends thereof with polyurethane or polypropylene which are exposed to the influence of light and heat, for example car upholstery, carpets or swimwear.

The compound of formula (1) is applied in the practice of this invention from an aqueous bath. The amount of compound used will depend on the substrate and on the desired stabilisation. Normally 0.01 to 10% by weight, preferably 0.1 to 5% by weight, based on the substrate, will be used.

The application of the novel compound can be made before, after or preferably during dyeing, by an exhaust process at liquor ratios of 1:5 to 1:500, preferably 1:10 to 1:50. The compound is conveniently added to the dyebath.

The novel compound can also be applied continuously by low application or high-temperature application systems.

In the continuous process, the liquor is conveniently applied to a pick-up of 30–400% by weight, preferably 75–250% by weight. For fixation of the dyes and the known and novel compounds the fibre material is subjected to a heat treatment. The fixation process can also be carried out by the cold pad-batch method.

The heat treatment is preferably carried out by steaming by treatment in a steamer with steam or superheated steam in the temperature range from 98°–105° C. for conveniently 1 to 7, preferably 1 to 5, minutes. The fixation of the dyes and the compound of formula (1) by the cold pad-bath method can be effected by storing the impregnated and preferably rolled up goods at room temperature (15° to 30° C.), conveniently for 3 to 24 hours, the cold batching time depending naturally on the type of dye used.

When the dyeing process and fixation is complete, the dyeings are rinsed and dried in conventional manner.

Dyeing is carried out in conventional manner conveniently with metal complex, anthraquinone or azo dyes and mixtures thereof. The metal complex dyes used are the known types, preferably the 1:2 chromium or 1:2 cobalt complexes of monoazo or disazo or azomethine dyes which are described in profusion in the literature. In addition to these dyes, dyes of other classes, such as disperse or also reactive dyes, may also suitably be used.

The invention is illustrated by the following Working and Use Examples in which parts and percentages are by weight. Unless otherwise indicated, the percentages of the ingredients of the individual dyebaths and treatment baths are based on the fibre material.

EXAMPLE 1

A solution of 1.75 g (14.3 mmol) of 1,3-propanesultone and 50 ml of acetone is added to a suspension of 4.9 g (14.3 mol) of the sodium salt of 2-ethoxy-2'-hydroxyoxalic acid dianilide (prepared by crystallisation of 2-ethoxy-2'-hydroxy-dianilide in aqueous sodium hydroxide) and 200 ml of acetone. After heating for 1 hour under reflux and subsequent cooling, the precipitate is filtered with suction and dried. Yield: 5.45 of the compound of formula

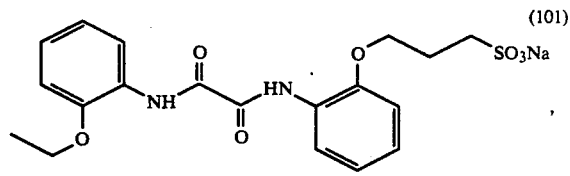

(101)

which is recrystallised from ethanol/water (8:2) to give a colourless substance.

Yield 86%; m.p. 236°–238° C.

Elemental analysis for $C_{19}H_{21}N_2O_7SNa \cdot 0{,}25\ H_2O$: found: 50.91% C; 4.83% H; 6.30% N; 7.08% S. calcd: 50.87% C; 4.75% H; 6.24% N; 7.14% S.

EXAMPLE 2

In accordance with the general procedure described in Example 1, 4.4 g (14.3 mmol) of the sodium salt of 2-ethyl-2'-hydroxyoxalic acid dianilide are reacted with 1.93 g (15.8 mmol) of 1,3-propanesultone. Recrystallisation from 45% ethanol gives 2.72 g of the colourless compound of formula

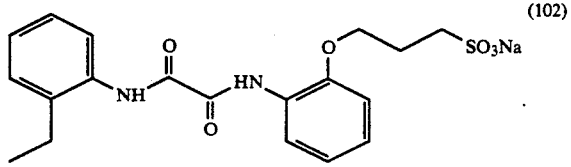

(102)

Yield 44%; m.p. 210°–212° C.

Elemental analysis for $C_{19}H_{21}N_2O_6SNa\cdot 0{,}25\ H_2O$: found: 52.78% C; 4.98% H; 6.58% N; 7.12% S. calcd: 52.71% C; 5.00% H; 6.47% N; 7.40% S.

EXAMPLE 3

8.02 g (38 mmol) of sodium 2-ethylsulfanilate are added at 100° C. to a melt of 9.48 g (40 mmol) of 2-ethoxyoxalic acid anilidemonoethyl ester and 5.44 of imidazole. The reaction mixture is heated for ½ hour to 110° C., then for 2 hours to 130° C. After cooling, the reaction mass is charged into 200 ml of water. The precipitate is filtered with suction, washed with 50 ml of ice-water and dried, giving 6.95 g of the compound of formula

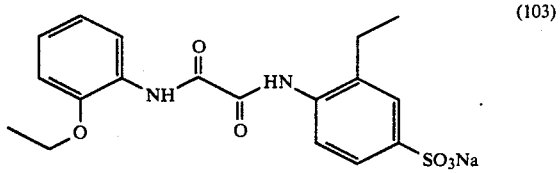

(103)

Yield: 44%; m.p. >300° C.

Elemental analysis for $C_{18}H_{19}N_2O_6SNa\cdot 0{,}25\ H_2O$: found: 51.6% C; 4.7% H; 6.8% N; 7.5% S. calcd: 51.60% C; 4.69% H; 6.68% N; 7.65% S.

EXAMPLES 4 to 29

Preparation of compounds (104) to (107), (110) to (114), (117) to (121) and (123) to (129)

In accordance with the general procedure of Example 2, 38 mmol of unsubstituted or substituted sulfanilic or metanilic acid are added at 100° C. to a melt of 40 mml of substituted oxalic acid anilide monoalkyl ester and 80 to 200 mmol of imidazole. The reaction mixture is heated for ½ hour to 110° C., then for 1 to 3 hours to 130° C. The completion of the reaction is determined by thin-layer chromatography. After cooling, the reaction mass is charged into c. 200 ml of water. The precipitate is filtered with suction, washed with water and dried. Acetone is used instead of water for working up compounds (104) and (105), and ethanol for working up compounds (106), (107) and (114). The yields are reported in Table I.

PREPARATION OF COMPOUND (116)

4.2 g (21.4 mmol) of a 30% methanolic solution of sodium methylate and 4.42 g (21.4) mmol) of sodium 3-chloro-2-hydroxypropanesulfonate are added to a solution of 4.51 g (14.25 mmol) of 2,5-dimethoxy-4'-hydroxyoxalic acid dianilide and 100 ml of dimethyl formamide. After stirring for 15 hours at 150° C., the precipitate (NaCl) is removed by filtration and the filtrate is concentrated by evaporation at 75° C./0.13 Pa. The residue is taken up in water. After addition of sodium chloride, the precipitated crude product is filtered with suction and recrystallised from dimethyl formamide/ethanol, giving 3.8 g of a white powder.

PREPARATION OF COMPOUND (109)

The compound is prepared in accordance with the general procedure for obtaining compound (116) by reacting 2-ethoxy-2'-hydroxyoxalic acid dianilide.

PREPARATION OF COMPOUNDS (108), (115) and (122)

The compounds are prepared in accordance with the general procedure described in Example 1.

PREPARATION OF THE STARTING COMPOUND FOR COMPOUNDS (115) and (116): 2,5-dimethoxy-4'-hydroxyoxalic acid dianilide 5.07 g (20 mmol) of 2,5-dimethoxyoxalic acid anilide monomethyl ester and 2 g (18 mmol) of 4-aminophenol are heated to 150° C. in the presence of catalytic amounts of boron trifluoride under a slight vacuum, and the alcohol formed is removed by distillation. After 5.5 hours the reaction mixture is cooled and 40 ml of ethanol are added. Crystallisation at −5° C. to give 3.4 g of crude product which is purified by washing with hot trichlorethylene.

m.p. 204°–205° C.

Elemental analysis for $C_{16}H_{16}N_2O_5$: found: 60.58% C; 5.19% H; 8.88% N. calcd: 60.75% C; 5.1% H; 8.86% N.

PREPARATION OF THE STARTING COMPOUND FOR COMPOUND (122): 2-methoxy-5-methyl-4'-hydroxyoxalic acid dianilide 8.3 g (41.5 mmol) of 4-hydroxyoxalic acid anilide monoethyl ester and 6.85 g (50 mmol) of 2-methoxy-5-methylaniline are heated under a slight vacuum to 130° C. and the alcohol formed is removed by distillation. After 7 hours the reaction mixture is cooled and and stirred with acetone. Insoluble by-product is removed by filtration, and the filtrate is poured into 130 ml of water to precipitate the product.

Yield: 6.27 g.

m.p. 189°–190° C.

Elemental analysis for $C_{16}H_{16}N_2O_4$: found: 64.0% C; 5.4% H; 9.4% N. calcd: 63.99% C; 5.3% H; 9.32% N.

TABLE I

| Compound No. | R | Yield [%] | Elemental analysis |
|---|---|---|---|

[Structure: 3-ethoxyphenyl-NH-C(=O)-C(=O)-NH-R]

| (104) | 4-SO₃Na-phenyl | 53 | 16H₁₅N₂O₆SNa<br>found: 49.68% C; 4.11% H; 7.28% N; 7.84% S<br>calcd: 49.74% C; 3.92% H; 7.25% N; 8.3% S |
| (105) | 3-CH₃-4-SO₃Na-phenyl | 62 | 17H₁₇N₂O₆SNa<br>found: 50.99% C; 4.14% H; 7.16% N; 7.90% S<br>calcd: 51.00% C; 4.28% H; 7.00% N; 8.01% S |
| (106) | 3-OCH₃-4-SO₃Na-phenyl | 81 | 17H₁₇N₂O₇SNa<br>found: 47.72% C; 4.32% H; 6.69% N; 7.40% S<br>cacld: 47.66% C; 4.31% H; 6.54% N; 7.48% S |
| (107) | 3-OC₂H₅-4-SO₃Na-phenyl | 71 | 18H₁₉N₂O₇SNa·½H₂O<br>found: 49.39% C; 4.52% H; 6.77% N; 7.35% S<br>calcd: 49.70% C; 4.51% H; 6.44% N; 7.37% S |
| (108) | 4-O-(CH₂)₃-SO₃Na-phenyl | 93 | 19H₂₁N₂O₇SNa<br>found: 51.01% C; 4.82% H; 6.35% N; 7.9% S<br>calcd: 51.35% C; 4.76% H; 6.30% N; 7.21% S |
| (109) | 2-(O-CH₂-CH(OH)-CH₂-SO₃Na)-phenyl | 37 | 19H₂₁N₂O₈SNa·H₂O<br>found: 47.70% C; 4.70% H; 6.00% N; 7.20% S<br>calcd: 47.69% C; 4.84% H; 5.89% N; 6.70% S |

[Structure: 2,5-dimethoxyphenyl-NH-C(=O)-C(=O)-NH-R]

| (110) | 4-SO₃Na-phenyl | 44 | 16H₁₅N₂O₇SNa<br>found: 47.48% C; 3.82% H; 6.95% N; 7.86% S<br>calcd: 47.76% C; 3.76% H; 6.96% N; 7.97% S |
| (111) | 3-CH₃-4-SO₃Na-phenyl | 52 | 17H₁₇N₂O₇SNa·½H₂O<br>found: 48.40% C; 4.10% H; 6.80% N; 7.40% S<br>calcd: 48.51% C; 4.19% H; 6.65% N; 7.61% S |

TABLE I-continued

Parent structure:

5-methyl-2-methoxy-phenyl—NH—C(=O)—C(=O)—NH—R

| Compound No. | R | Yield [%] | Elemental analysis |
|---|---|---|---|
| (112) | 2-ethyl-4-sulfonato phenyl (C₂H₅ ortho, SO₃Na para) | 35 | 18H19N2O6SNa.½H2O<br>found: 51.60% C; 4.70% H; 6.80% N; 7.50% S<br>calcd: 51.60% C; 4.69% H; 6.68% N; 7.65% S |
| (113) | 2-methoxy-4-sulfonato phenyl (OCH₃, SO₃Na) | 69 | 17H17N2O8SNa<br>found: 47.02% C; 4.06% H; 6.86% N; 7.05% S<br>calcd: 47.22% C; 3.96% H; 6.47% N; 7.41% S |
| (114) | 2-ethoxy-4-sulfonato phenyl (OC₂H₅, SO₃Na) | 87 | 18H19N2O8SNa<br>found: 48.00% C; 4.30% H; 6.60% N; 6.80% S<br>calcd: 48.43% C; 4.29% H; 6.28% N; 7.18% S |
| (115) | 4-(3-sulfonatopropoxy)phenyl —O—(CH₂)₃—SO₃Na | 98 | 19H21N2O8SNa.½H2O<br>found: 48.53% C; 4.50% H; 5.98% N; 6.79% S<br>calcd: 48.61% C; 4.72% H; 5.96% N; 6.82% S |
| (116) | 4-(2-hydroxy-3-sulfonatopropoxy)phenyl —O—CH₂—CH(OH)—CH₂—SO₃Na | 56 | 19H21N2O9SNa<br>found: 47.87% C; 4.64% H; 6.02% N; 6.64% S<br>calcd: 47.90% C; 4.44% H; 5.88% N; 6.73% S |

Structure:

CH₃—(5-methyl, 2-methoxy phenyl)—NH—C(=O)—C(=O)—NH—R

| Compound No. | R | Yield [%] | Elemental analysis |
|---|---|---|---|
| (117) | 4-sulfonatophenyl | 40 | 16H15N2O6SNa<br>found: 49.40% C; 4.00% H; 7.30% N; 8.30% S<br>calcd: 49.74% C; 3.91% H; 7.25% N; 8.29% S |
| (118) | 2-methyl-4-sulfonato phenyl (CH₃, SO₃Na) | 62 | 17H17N2O6SNa.½H2O<br>found: 50.20% C; 4.40% H; 7.10% N; 8.00% S<br>calcd: 50.20% C; 4.38% H; 6.89% N; 7.89% S |
| (119) | 2-ethyl-4-sulfonato phenyl (C₂H₅, SO₃Na) | 35 | 18H19N2O6SNa.½H2O<br>found: 51.76% C; 4.72% H; 6.82% N; 7.65% S<br>calcd: 51.60% C; 4.69% H; 6.68% N; 7.65% S |
| (120) | 2-methoxy-4-sulfonato phenyl (OCH₃, SO₃Na) | 38 | 17H17N2O7SNa.2¾H2O<br>found: 46.57% C; 4.59% H; 6.59% N; 7.30% S<br>calcd: 46.52% C; 4.48% H; 6.38% N; 7.30% S |

TABLE I-continued

| Compound No. | R | Yield [%] | Elemental analysis |
|---|---|---|---|
| (121) | 3-methyl-4-ethoxy-benzenesulfonate (O-C₂H₅ ortho to CH₃, SO₃Na para) | 68 | 18H₁₉N₂O₇SNa·½H₂O<br>found: 49.27% C; 4.60% H; 6.49% N; 7.34% S<br>calcd: 49.20% C; 4.59% H; 6.37% N; 7.29% S |
| (122) | 4-methylphenyl O—(CH₂)₃—SO₃Na | 69 | 19H₂₁N₂O₇SNa·½H₂O<br>found: 51.00% C; 4.80% H; 6.30% N; 7.20% S<br>calcd: 51.35% C; 4.76% H; 6.30% N; 7.21% S |

3,5-dimethoxyphenyl-NH-C(O)-C(O)-NH-R

| (123) | 4-methyl-benzenesulfonate (CH₃, SO₃Na) | 58 | 17H₁₇N₂O₇SNa<br>found: 48.70% C; 4.10% H; 6.80% N; 7.60% S<br>calcd: 49.00% C; 4.12% H; 6.73% N; 7.70% S |
| (124) | 4-ethyl-benzenesulfonate (C₂H₅, SO₃Na) | 46 | 18H₁₉N₂O₇SNa<br>found: 50.20% C; 4.40% H; 6.60% N; 7.50% S<br>calcd: 50.23% C; 4.45% H; 6.51% N; 7.45% S |
| (125) | 4-methoxy-benzenesulfonate (OCH₃, SO₃Na) | 75 | 17H₁₇N₂O₈SNa·½H₂O<br>found: 46.63% C; 4.06% H; 6.55% N; 7.14% S<br>calcd: 46.73% C; 4.03% H; 6.41% N; 7.33% S |
| (126) | 4-ethoxy-benzenesulfonate (OC₂H₅, SO₃Na) | 40 | 18H₁₉N₂O₈SNa<br>found: 48.29% C; 4.42% H; 6.41% N; 7.06% S<br>calcd: 48.43% C; 4.29% H; 6.28% N; 7.18% S |

3-methyl-5-methoxyphenyl-NH-C(O)-C(O)-NH-R

| (127) | 4-methyl-benzenesulfonate (CH₃, SO₃Na) | 43 | 17H₁₇N₂O₆SNa<br>found: 50.80% C; 4.4% H; 7.2% N; 8.20% S<br>calcd: 51.00% C; 4.28% H; 7.00% N; 8.01% S |
| (128) | 4-methoxy-benzenesulfonate (OCH₃, SO₃Na) | 55 | 17H₁₇N₂O₇SNa<br>found: 49.10% C; 4.20% H; 7.00% N; 7.70% S<br>calcd: 49.04% C; 4.12% H; 6.73% N; 7.70% S |

TABLE I-continued

| Compound No. | R | Yield [%] | Elemental analysis |
|---|---|---|---|
| (129) | 2-methyl-4-sulfo-phenyl ether with OC$_2$H$_5$ (SO$_3$Na) | 73 | 18H$_{19}$N$_2$O$_7$SNa.½H$_2$O<br>found: 49.60% C; 4.52% H; 6.54% N; 7.32% S<br>calcd: 49.71% C; 4.40% H; 6.44% N; 7.37% S |

USE EXAMPLES

EXAMPLE 30

Two 10 g samples of PA 6 knitgoods are dyed in an ®AHIBA dyeing machine at a liquor ratio of 1:25. Both dyebaths contain the following ingredients: 0.5 g/l of monosodium phosphate, 1.5 g/l of disodium phosphate and the dyes of formulae (I) and (II). All ingredients are dissolved before being added.

The textile materials are put into these liquors, which have been warmed to 40° C., and treated at this temperature for 10 minutes. The liquors are then heated at 2° C./minute to 95° C. After a dyeing time of 20 minutes at 95° C., 2% of acetic (80%) is added and dyeing is continued for another 25 minutes. After cooling to 60° C., the goods are rinsed with cold water, centrifuged, and then dried at 120° C. for 2 minutes.

The dyeings are tested for their fastness to hot light according to DIN 75 202 (FAKRA). To determine the photochemical stabilisation, the dyed samples measuring 12×14.5 cm are mounted on cardboard and irradiated for 216 hours (=3 FAKRA cycles). The results are reported in Table 2.

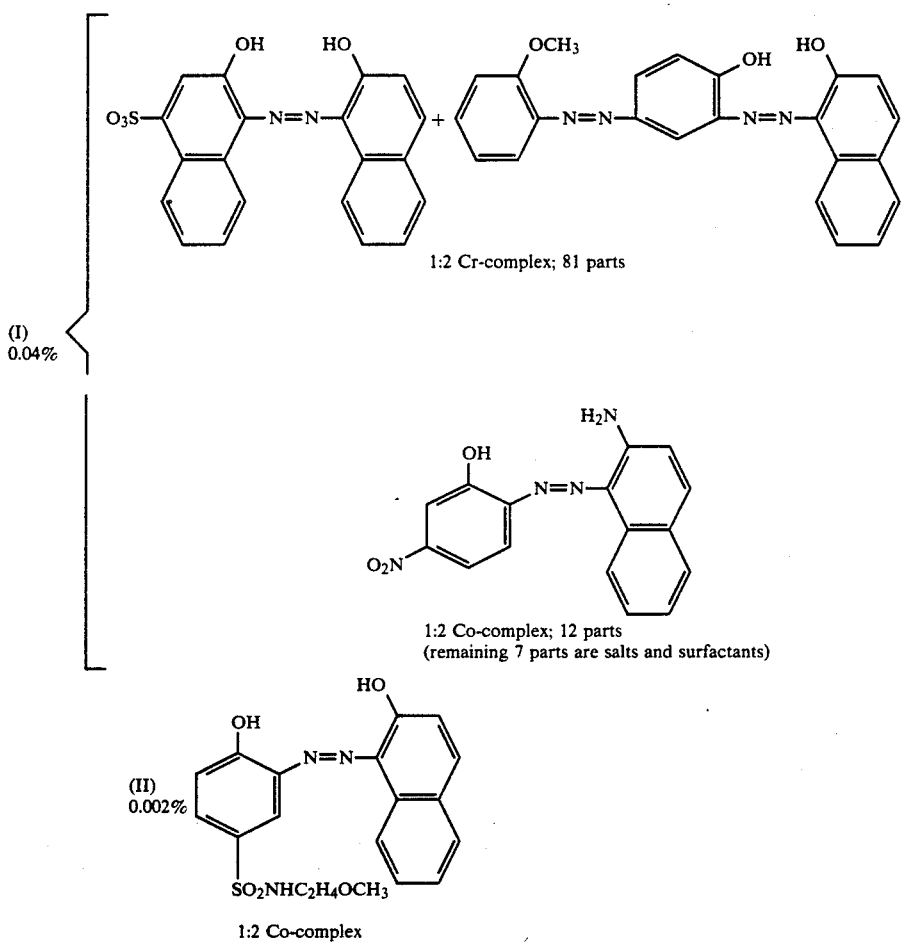

Whereas liquor 1 contains no further ingredients, 1% of the compound of formula (101), dissolved in water, is added to liquor 2.

TABLE 2

| Addition to dyebath | Lightfastness 144 h FAKRA | Tear strength/stretch [%] after 216 h FAKRA light | |
|---|---|---|---|
| none | 1H* | 12.3 | 33.3 |
| +1% of compound of formula (101) | 2 | 42.8 | 53.7 |

*Sample has only insignificant tear strength

It is evident that dyeings of markedly enhanced properties are obtained with the UV absorber.

EXAMPLE 31

Three liquors are prepared as described in Example 30, but without dye (blank dyeings):
liquor 1 contains no further ingredients
liquor 2 contains 1% of the compound of formula

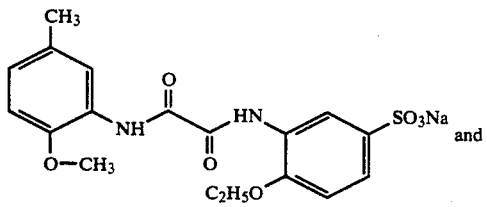
(126)

liquor 3 contains 1% of the compound of formula

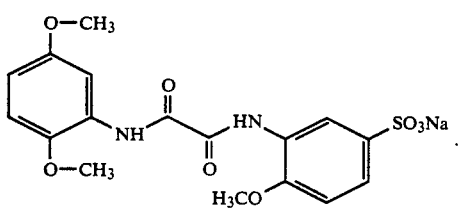
(113)

The pretreated tricot material is treated as described in Example 30, then exposed for 216 h to FAKRA light and, finally, tested for its stability according to Ser. No. 198 461. The results are reported in Table 3.

TABLE 3

| Addition to dyebath | Tear strength/stretch [%] after 216 h FAKRA light | |
|---|---|---|
| liquor 1: none | 4.3 | 17.1 |
| liquor 2: +1% of compound 1 of formula (126) | 24.1 | 39.6 |
| liquor 3: +1% of compound of formula (113) | 27.7 | 40.7 |

EXAMPLE 32

4 samples of PA 66 tricot are prepared, using a dyebath as described in Example 30, except that
liquor 1 contains no further ingredients (blank dyeing)
liquor 2 contains 1% of the compound of formula

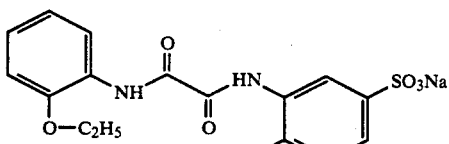
(107)

liquor 3 contains 1% of the compound of formula

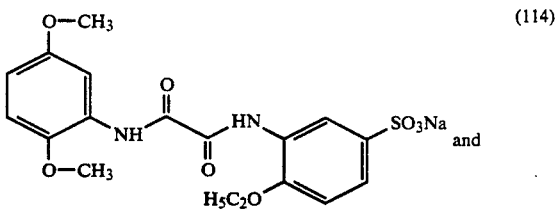
(114)

liquor 4 contains 1% of the compound of formula

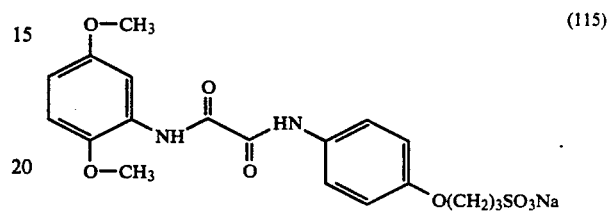
(115)

Dyeing and testing are carried out as in Example 30. The results are reported in Table 4.

TABLE 4

| Addition to dyebath | Lightfastness 144 h FAKRA | Tear strength/stretch [%] after 216 h FAKRA light | |
|---|---|---|---|
| liquor 1: none | <<1H | 4.3 | 16.8 |
| liquor 2: +1% of compound of formula (107) | 1–2 H | 16.9 | 30.6 |
| liquor 3: +1% of compound of formula (114) | 1–2 H | 35.4 | 40.9 |
| liquor 4: +1% of compound of formula (115) | 1–2 H | 31.5 | 39.5 |

*Material decomposes

What is claimed is:

4. An oxalic acid diarylamide of formula

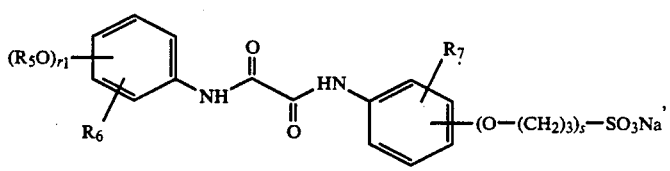
(2)

wherein
R$_4$ is C$_1$–C$_{12}$alkyl or C$_1$–C$_5$alkoxy, and
R$_1$, R$_2$, M and r are as defined in claim 1.

5. An oxalic acid diarylamide of formula (3)

wherein
R$_5$ is C$_1$–C$_3$alkyl,
R$_6$ is hydrogen or C$_1$–C$_3$alkyl,
R$_7$ is hydrogen or C$_1$–C$_3$alkoxy
r$_1$ is 0, 1 or 2, and
s is 0 or 1.

6. An oxalic acid diarylamide according to claim 5, wherein
R$_5$ is ethyl and
R$_6$ is hydrogen or ethyl.

7. An oxalic acid diarylamide of formula

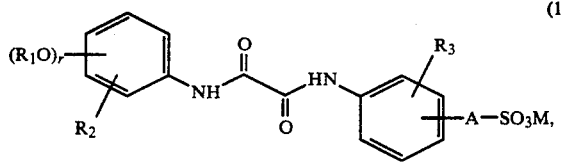

(4)

1. A water-soluble, asymmetrical oxalic acid diarylamide of the formula

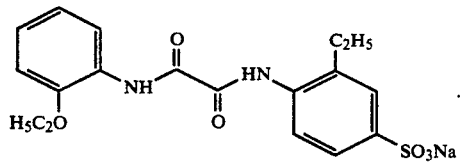

(1)

wherein the substituents
R$_1$ are each independently of the other unsubstituted or hydroxy- or alkoxy-substituted-C$_1$–C$_5$alkyl or unsubstituted or C$_1$–C$_5$alkyl-substituted benzyl,
R$_2$ is hydrogen, halogen, C$_1$–C$_{12}$alkyl or phenyl-C$_1$–C$_5$alkyl,
R$_3$ is hydrogen, halogen, C$_1$–C$_{12}$alkyl, phenyl-C$_1$–C$_5$alkyl or C$_1$–C$_5$alkoxy,
A is —O—CH$_2$—CH$_2$—CH$_2$—  or  —O—CH$_2$—CH—CH$_2$—,
$\qquad\qquad\qquad\qquad\qquad\qquad\quad$ |
$\qquad\qquad\qquad\qquad\qquad\qquad\quad$ OH M is hydrogen or an alkali metal, and
r is 2, 1 or 0.

2. A water-soluble, asymmetrical oxalic acid diarylamide of claim 1 wherein A is —O—CH$_2$—CH$_2$—CH$_2$—.

3. A water-soluble, asymmetrical oxalic acid diarylamide of claim 1 wherein A is

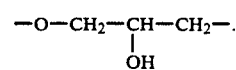

* * * * *